(12) United States Patent
Gutierrez Morales

(10) Patent No.: US 9,601,031 B1
(45) Date of Patent: Mar. 21, 2017

(54) MEDICAL ATTACHMENT DEVICE POSITION DETECTION SYSTEM AND METHOD OF USE THEREOF

(71) Applicant: Christian Raul Gutierrez Morales, Miramar, FL (US)

(72) Inventor: Christian Raul Gutierrez Morales, Miramar, FL (US)

( * ) Notice: Subject to any disclaimer, the term of this patent is extended or adjusted under 35 U.S.C. 154(b) by 0 days.

(21) Appl. No.: 15/163,421

(22) Filed: May 24, 2016

Related U.S. Application Data

(63) Continuation-in-part of application No. 14/844,574, filed on Sep. 3, 2015.

(51) Int. Cl.
*G09B 23/28* (2006.01)
*G09B 5/04* (2006.01)
*A61B 7/02* (2006.01)
*H04R 1/02* (2006.01)

(52) U.S. Cl.
CPC ............... *G09B 23/28* (2013.01); *A61B 7/02* (2013.01); *G09B 5/04* (2013.01); *H04R 1/028* (2013.01)

(58) Field of Classification Search
CPC ....................................................... G09B 23/28
USPC ........................................................ 434/267
See application file for complete search history.

(56) References Cited

U.S. PATENT DOCUMENTS

2016/0051164 A1* 2/2016 Derichs ................. G01R 33/02
600/409

* cited by examiner

*Primary Examiner* — Xuan Thai
*Assistant Examiner* — Robert P Bullington
(74) *Attorney, Agent, or Firm* — The Concept Law Group, P.A.; Scott D. Smiley; Erin A. Martin

(57) ABSTRACT

A medical attachment device position detection system for use during medical training including a processor and a medical attachment device communicatively coupled to the processor, a first magnetometer coupled to the medical attachment device and configured to detect a first angle, and a second magnetometer configured to detect a second angle. The second magnetometer is communicatively coupled to the processor. The processor is operably configured to compare a relationship of the first angle relative to the second angle to determine a position of the medical attachment device relative to a subject.

14 Claims, 12 Drawing Sheets

MEDICAL ATTACHMENT DEVICE POSITION DETECTION SYSTEM AND METHOD OF USE THEREOF

CROSS-REFERENCE TO RELATED APPLICATION

This application is a continuation-in-part and claims priority to U.S. application Ser. No. 14/844,574 filed Sep. 3, 2015, the entirety of which is incorporated by reference.

FIELD OF THE INVENTION

The present invention relates generally to auscultation training, and, more particularly, relates to a medical attachment device position detection system and method of use thereof during auscultation training.

BACKGROUND OF THE INVENTION

It is well known that auscultation training is important to medical education. Auscultation is the act of listening to sounds from the heart, lungs, or other body parts typically with a stethoscope, as a part of medical diagnosis. During auscultation training, standardized patients are often used as they provide unsurpassed realism when training for real patient encounters. Generally speaking, standardized patients are actors trained to mimic a variety of symptoms, signs, psychiatric conditions, and the like. Unfortunately, there is a limited scope on what standardized patients can provide on physical examination, as most standardized patients do not have abnormal physical findings. This problem is especially evident when the standardized patient is attempting to simulate pathologies involving distinct findings, such as heart murmurs, abnormal lung, or abnormal abdominal sounds.

Systems that improve upon auscultation training are well known. For example, stethoscope-shaped devices exist having an embedded speaker which plays pre-recorded digital audio files at the command of an instructor observing the location of the stethoscope-shaped device with respect to a simulated patient. In some instances, the speaker may emit sound using a remote control. This does not allow a trainee, e.g., a medical student, to utilize his or her own personal stethoscope. Moreover, the instructor must monitor the location of the stethoscope and control the sound at the appropriate time, as there is no tracking system provided to perform such monitoring.

In another example, the simulated stethoscope plays pre-recorded digital sounds and the stethoscope head includes an embedded Radio-frequency identification (RFID) tag reader. The simulated patient has RFID tags placed in the physical location in which the trainee is intended to auscultate. Unfortunately, the RFID tags placed upon the simulated patient take away from the realism of the training. In addition, the RFID tags inform the trainee exactly where to place the stethoscope's head, which defeats a major part of the evaluation and teaching objectives of providing a real life scenario.

Another known auscultation training system requires the simulation patient to wear a garment having one or more markings, e.g., RFID tags. When performing auscultation training, a sound-generating device is attached to the stethoscope diaphragm. As the sound-generating device hovers over a sensor embedded in the garment at the location of the marking, the sound-generating device plays an appropriate physiological sound. Obviously, the realism of the scenario is reduced because the markings show the trainee exactly where to place the stethoscope diaphragm and sound-generating device. Moreover, the simulated patient is forced to wear a garment that may be uncomfortable and which must be tailored to fit the simulated patient.

Other known auscultation training systems include a specialized stethoscope, an infrared camera for stethoscope location tracking, and a prompt screen for generating breathing synchronization. In use, a single infrared light-emitting diode located on top of the stethoscope head is tracked by a static infrared camera, which is connected to a main computer system. Unfortunately, stethoscope location tracking will not work if the trainee steps into the camera's line-of-sight or if the stethoscope is not facing the infrared camera. In order to generate breathing synchronization, the standardized patient paces his or her breathing cycle to mirror the signal shown on a prompt screen connected to a main computer system. For proper performance of breathing synchronization, the simulated patient must be able to view the prompt screen and therefore must remain facing the screen during examination. Obviously, such restrictions would greatly interfere with common physical examination practices taught to medical professionals. In addition, these systems may be expensive to implement and maintain.

Therefore, a need exists to overcome the problems with the prior art as discussed above.

SUMMARY OF THE INVENTION

The invention provides a medical attachment device position detection system and method of use for auscultation training that overcomes the hereinafore-mentioned disadvantages of the heretofore-known devices and methods of this general type and that provides a system that determine a position of a medical attachment device on various locations of a subject in order to effectively and efficiently provide a realistic scenario for a trainee during auscultation training.

With the foregoing and other objects in view, there is provided, in accordance with the invention, a medical attachment device position detection system for use during medical training including a processor, a medical attachment device communicatively coupled to the processor, a first magnetometer coupled to the medical attachment device, the first magnetometer configured to produce data associated with a first angle, and a second magnetometer configured to produce data associated with a second angle. The second magnetometer may be communicatively coupled to the processor and the processor may be operably configured to compare a relationship of the first angle relative to the second angle to determine a position of the medical attachment device relative to a subject.

In accordance with another feature of the present invention, the medical attachment device is a stethoscope having an orientation sensor coupled thereto.

In accordance with a further feature of the present invention, the second magnetometer is a 3-axis magnetometer.

In accordance with another feature, an embodiment of the present invention includes the processor and the second magnetometer each housed within an electronic device.

In accordance with a further feature of the present invention, the medical attachment device position detection system includes a speaker coupled to the medical attachment device.

In accordance with a further feature of the present invention, the position of the medical attachment device relative to the subject is at least one of anterior to the subject, posterior to the subject, disposed on a right side of the subject, and disposed on a left side of the subject.

In accordance with another further feature of the present invention, the first angle is between approximately −180° to +180°.

In accordance with the present invention, a method of detecting a position of a medical attachment device relative to a subject is disclosed, the method including providing a medical attachment device position detection system having a processor, a medical attachment device communicatively coupled to the processor, a first magnetometer coupled to the medical attachment device, the first magnetometer configured to produce data associated with a first angle and a second magnetometer configured to produce data associated with a second angle. The second magnetometer may be communicatively coupled to the processor and the processor may be operably configured to compare a relationship of the first angle relative to the second angle to determine a position of the medical attachment device relative to the subject. The method may include positioning the first magnetometer in close proximity to the subject, positioning the second magnetometer in close proximity to the subject, and comparing the first angle from the first magnetometer to the second angle from the second magnetometer to obtain a position of the medical attachment device.

In accordance with another further feature of the present invention, the second magnetometer is a 3-axis magnetometer.

In accordance with a further feature of the present invention, the processor and the second magnetometer are each housed within an electronic device.

In accordance with a further feature of the present invention, the method may include positioning the electronic device in close proximity to a side of the subject.

In accordance with another feature of the present invention, the method may include positioning the medical attachment device relative to at least one of anterior to the subject, posterior to the subject, on a right side of the subject, and on a left side of the subject.

In accordance with yet another feature of the present invention, the medical attachment device is a stethoscope having speaker coupled thereto, the speaker communicatively coupled to a sound database including a plurality of sounds operably configured to simulate a medical condition.

In accordance with a further feature of the present invention, the method may include positioning the medical attachment device within a first position relative to the subject, causing the speaker to emit a first sound from the sound database, the first sound corresponding to the first position, positioning the medical attachment device within a second position relative to the subject, and causing the speaker to emit a second sound from the sound database, the second sound corresponding to the second position.

In accordance with a further feature of the present invention, the medical attachment device is a stethoscope having an orientation sensor coupled thereto.

In accordance with a further feature of the present invention, the method may include providing a plurality of coordinate regions corresponding to the position of the medical attachment device.

Although the invention is illustrated and described herein as embodied in a medical attachment device position detection system and method of use thereof, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the subject from the subject's waist toward the subject's neck. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
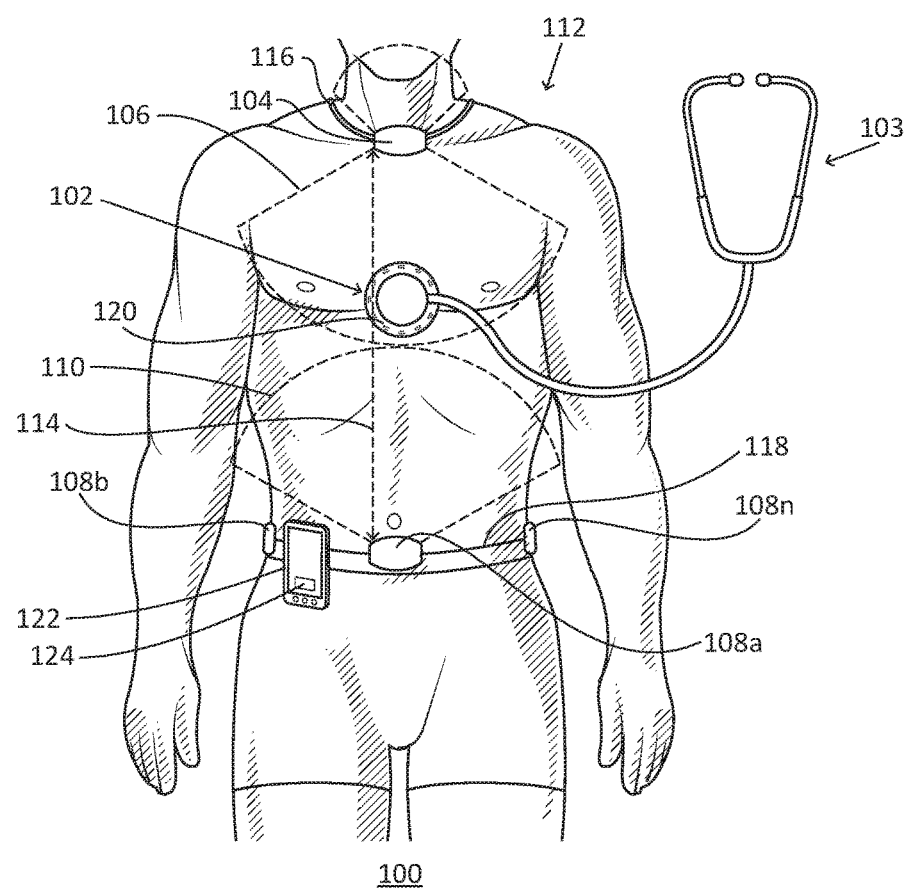
FIG. 1 is an elevational front view of a tracking system for tracking a medical attachment device within a tracking area relative to a subject and the subject in accordance with an embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient tracking system for tracking a medical attachment device relative to a subject, e.g., a simulated patient, which offers a realistic training scenario during auscultation training. The present invention is primarily designed for use during auscultation training, however may be used in other settings as well. Embodiments of the invention provide a plurality of reflectors on the subject that define at least one tracking region along the subject's frame. The reflectors may be located, for example, on the subject's necklace and belt. Advantageously, the necklace and the belt add to the realism of the scenario as these items are commonly worn in everyday settings. The medical attachment device may include a reflector sensor configured to determine, in combination with a processor, a location of the medical attachment device relative to one or more of the reflectors. In one embodiment, the reflector sensor includes a plurality of light emitters which emit a light signal, in a direction toward the reflectors. The reflectors reflect the light signal in a direction toward a plurality of photodetectors disposed on the medical attachment device. Advantageously, using data generated by the photodetectors, the processor can determine a distance between the medical attachment device and at least one reflector. A biological sound corresponding to the appropriate location on the subject may then be transmitted from the processor through a speaker on the medical attachment device representative of real cardiac and respiratory events. In one non-limiting embodiment, the medical attachment device may be coupled to a stethoscope.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. The first example of a tracking system 100, as shown in FIG. 1, includes a trackable medical attachment device 102 that may be tracked within a tracking area that includes at least one tracking region. In one embodiment, the medical attachment device 102 is a disc, sized and shaped to couple to a diaphragm of a stethoscope 103. In such advantageous embodiments, trainees operating the tracking system 100 may use their own medical diagnostic tool during auscultation training. The medical attachment device 102 is not limited to being shaped as a disc; rather, it may be provided in various other sizes and shapes complimentary to the stethoscope 103 or another medical diagnostic tool, such as a probe. The term "medical diagnostic tool" is defined herein as an instrument, apparatus, or similar article used to diagnose, prevent, or treat disease or other conditions. In other embodiments, the medical attachment device 102 may be the medical diagnostic tool having the components of the tracking system 100 permanently coupled thereto.

In one embodiment, the tracking area is defined by a first reflector 104 defining a first tracking region 106 located on an anterior region of a subject 112. The location of the first tracking region 106 may vary according to an angle of the first reflector 104. In one non-limiting embodiment, the first tracking region 106 spans approximately from the subject's 112 neck to the subject's 112 mid-torso. The subject's 112 mid-torso generally includes the area within approximately 2-4 inches above the subject's 112 naval. In other embodiments the first tracking region 106 may be located outside of this range.

In another embodiment, the tracking region is defined by a second reflector 108 defining a second tracking region 110 located on an anterior region of the subject 112. The second tracking region 110 may vary according to an angle of the second reflector 108. In one embodiment, the second tracking region 110 spans approximately from the subject's 112 mid-torso to 1-3 inches below the subject's 112 waistline. In other embodiments the second tracking region 110 may be located outside of this range. In another embodiment, the tracking area is defined by both the first tracking region 106 and the second tracking region 110.

In other embodiments, the tracking area may be defined by one or more reflectors 108b, 108n, disposed on either or both sides of the subject 112. The present invention may include a plurality of reflectors 108a-n coupled to the subject 112, where the indicator "a-n" is intended to represent any number of items, with "a" indicating 1 and "n" indicating any number greater than 1. Said another way, the number of reflectors 104, 108 may vary and the tracking system 100 is not limited to any particular quantity. In a preferred embodiment, the subject 112 is a simulated patient, a standard patient, or another person participating in auscultation training. In another embodiment, the subject 112 may be a mannequin, although a living person is preferred to provide a more realistic setting during auscultation training. FIG. 1 depicts the first and second reflectors 104, 108, located a distance 114 from each other. The distance 114 may vary according to the height of the subject 112, the placement of the reflectors 104, 108, etc.

Figure 2:
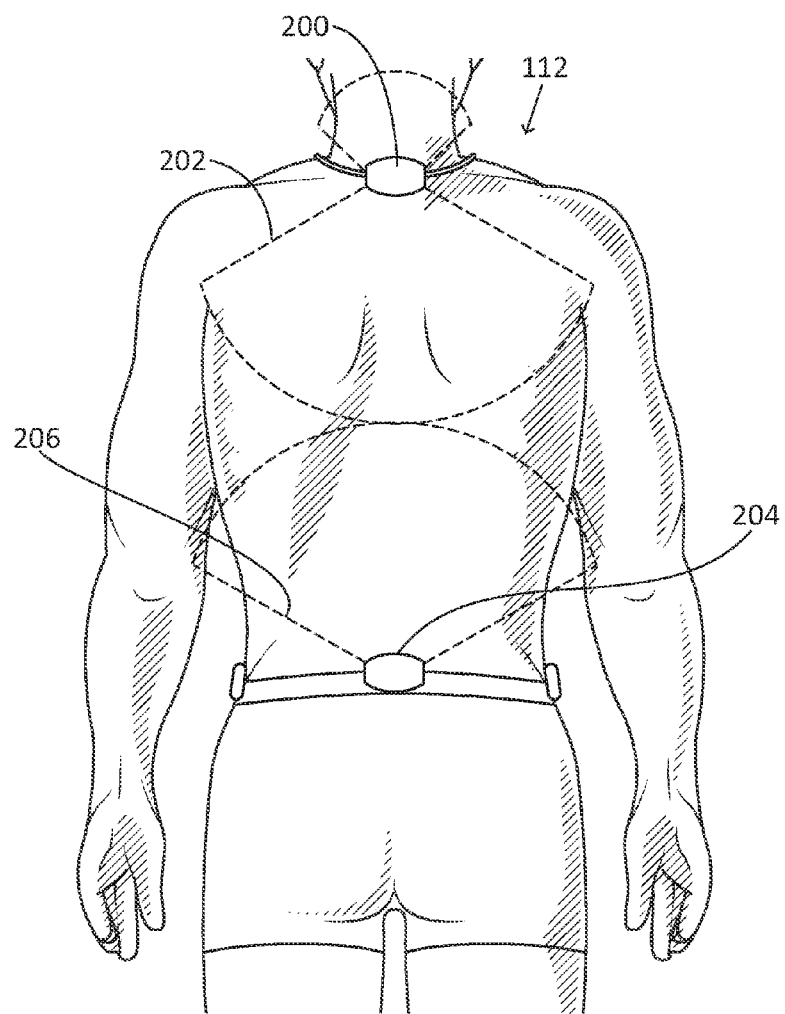
FIG. 2 is an elevational rear view of the subject of FIG. 1 depicting the tracking area in accordance with an embodiment of the present invention.

With brief reference to FIG. 2, the tracking area may include a third reflector 200 defining a third tracking region 202 and a fourth reflector 204 defining a fourth tracking region 206 on a posterior region of the subject 112. The third and fourth reflectors 200, 204 and the third and fourth regions 202, 206 will be described generally as having identical or nearly identical features as the first and second reflectors 104, 108 and the first and second tracking regions 106, 110. In other embodiments, the tracking area may include additional regions defined by additional reflectors.

With reference again to FIG. 1, generally speaking, the first and second reflectors 104, 108 are passive components configured to reflect the light signal from at least one light emitter 300 (FIG. 3) disposed on the medical attachment device 102, as will be explained in further detail herein. In one embodiment, the first and second reflectors 104, 108 may be the subject's 112 skin or another portion of the subject's 112 body. The first and second reflectors 104, 108 are not limited to reflecting a light signal; rather, in other embodiments, the first and second reflectors 104, 108 may reflect sound waves, lasers, or another type of electromagnetic or mechanical wave signal. The first and second reflectors 104, 108 may include a mirror or another reflective surface configured to reflect the light signal, or another type of electromagnetic or mechanical wave signal, emitted by the light emitter 300 or another type of signal emitter. The reflectors 104, 108 may be curved, rectangular, square, oval, or any other shape.

The first and second reflectors 104, 108 may be coupled directly or indirectly to the subject 112. In one non-limiting embodiment, the first and second reflectors 104, 108 may be coupled to the subject using a bonding agent, e.g., an adhesive, applied to a rear portion of the first and second reflectors 104, 108 (not shown). FIG. 1 depicts the first reflector 104 coupled to a first article of clothing 116, e.g., a necklace, and the second reflector 108 coupled to a second article of clothing 118, e.g. a belt, worn by the subject 112. In one embodiment, as opposed to the first and second reflectors defining the tracking regions 106, 110, the first and second articles of clothing 116, 118 can be said to define the first and second tracking regions 106, 110, respectively. The first article of clothing 116 and the second article of clothing 118 may be the same or a different type of clothing from one another. The necklace and the belt depicted in FIGS. 1 and 2 are provided by way of example and the first and second articles of clothing 116, 118, are in no way limited to the necklace and the belt.

Advantageously, the reflectors 104, 108, being attached to the articles of clothing 116, 118 enhances the realism of the auscultation training sessions because the trainee operating the medical attachment device 102 is not provided with predisposed visible locations for placement of the medical attachment device 102. Said another way, the tracking system 100 presents a significant advantage over prior art devices that illustrate where the trainee is to place a medical diagnostic device, e.g., a stethoscope, because the trainee must learn where to place the medical diagnostic device relative to the subject 112 independently, as which would occur in a realistic, non-training scenario. In such realistic scenario, it is common for a subject to wear an article of clothing, such as the necklace and/or the belt depicted in FIG. 1.

Figure 3:
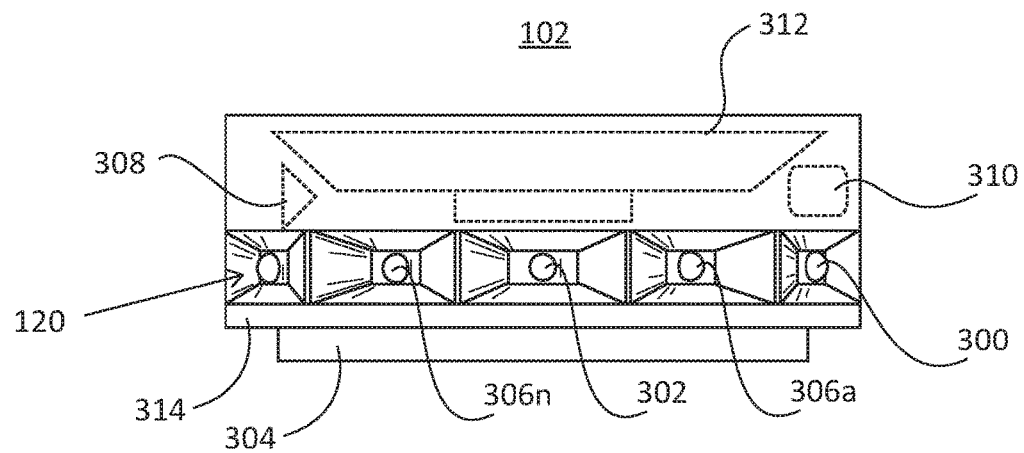
FIG. 3 is an elevational side view of the medical attachment device of the tracking system of FIG. 1.

With reference now to FIG. 3, one exemplary embodiment of the medical attachment device 102 is shown in a side elevational view. In one embodiment, the medical attachment device 102 includes a reflector sensor 120 fixedly or removably coupled thereto. In one embodiment, the reflector sensor 120 includes a first light emitter 300 and a second light emitter 302. The number of light emitters may vary and the present invention is not limited to any particular quantity. In one embodiment, the light emitters 300, 302 are infrared light emitting diodes (LEDs). Advantageously, in embodiments using infrared light emitting diodes, the light emitters 300, 302 can be easily and inexpensively replaced as needed.

With reference to FIGS. 1 and 3, when the medical attachment device 102, is placed in close proximity of the subject 112, an activation device 304 may be activated to start the location tracking process. The term "close proximity" is defined herein as touching the subject 112 or within 5 inches of the subject 112. The activation device 304 may operate through a mechanical, resistive, capacitive, or optical system configured to detect when the medical attachment device 102 is placed in close proximity to the subject 112.

Following activation of the activation device 304, the light emitters 300, 302 emit signals, e.g., light signals, in a direction toward the reflectors 104, 108. More specifically, in one exemplary embodiment, the light signals are emitted from the light emitters 300, 302 simultaneously, with the tracking system 100 cycling through at least six possible combinations, in embodiments having six light emitters. The light signals then reflect from the reflectors 104, 108 in a direction toward a plurality of photodetectors 306a-n located adjacent the first and second light emitters 300, 302. The reflective characteristics of the first and second reflectors 104, 108 minimize the loss of the light signal when reflected, significantly extending the range of the reflector sensor 120. The photodetectors 306a-n are not limited to placement adjacent the light emitters 300, 302; rather, in one embodiment, the photodetectors 306a-n may be disposed anywhere on the medical attachment device 102. In other embodiments, the plurality of photodetectors 306a-n may be disposed on the first article of clothing 116 and the second article of clothing 118 and/or the subject 112, with the reflectors 108a-n being disposed on the medical device 102.

In one embodiment, the photodetectors 306a-n are infrared phototransistors. In one embodiment, the photodetectors 306a-n are configured to sense the energy emitted by the light emitters 300, 302. The photodetectors 306a-n may then generate in response to the energy, a signal current proportional to the intensity of the light emitted by the light emitters 300, 302. The intensity of the light is used to determine the distance of the medical attachment device 102 from at least one of the reflectors 104, 108 and to determine which side of the medical attachment device 102 is closest to the reflectors 104, 108. Advantageously, rather than require the subject 112 to face a screen or monitor throughout the auscultation training, the subject 112 may be positioned at any angle or position in a room during use of the tracking system 100, which further enhances the realism of the auscultation training.

In one embodiment, the tracking system 100 includes a comparator 308 for comparing the data gathered by the plurality of photodetectors 306a-n. For example, the comparator 308 may compare the intensity of a signal strength of the first light signal and the second light signal to determine the location of the medical attachment device 102 relative to the subject 112. More specifically, in one non-limiting embodiment, the photodetectors 306a-n may be operably configured to measure a distance between the photodetectors 306a-n and the reflectors 104, 108 by measuring the strength of a light signal at the photodetectors 306a-n after it has been emitted by the first light emitter 300 and the second light emitter 302, and reflected back from the reflectors 104, 108. In other embodiments, the detectors 306a-n may be operably configured to measure a distance between the detectors 306a-n and the reflectors 104, 108 by measuring the time it takes for a signal, e.g., sound waves, to reflect from the reflectors 104, 108 and return to the detectors 306a-n. Comparing the signal strengths among the photodetectors 306a-n allows the tracking system 100 to determine which photodetector 306a-n is closest to which reflector 104, 108. Said another way, through the comparison of the signal strengths and/or timing, i.e., data provided from the photodetectors 306a-n, the reflector sensor 120 is operable to integrate the first and second reflectors 104, 108 in combination with a processor 122 to determine a location of the medical attachment device 102 relative to the subject 112.

FIG. 1 depicts the processor 122 as a smartphone attached to the belt of the subject 112. In other embodiments, the processor 122 may be a tablet, a personal digital assistant, a computer, or the like. In one embodiment, the processor 122 is coupled to the belt, with a camera disposed on the processor 122 facing away from the subject 112. In other embodiments, the processor 122 may be disposed within a pocket coupled to the subject 112 or may be coupled in another manner to the subject 112. In embodiments in which the tracking system 100 includes a wireless connection, the medical attachment device 102 includes a wireless transmitter/receiver 310 communicatively coupled to the processor 122. The wireless transmitter/receiver 310 may operate using a radio transmitter, Bluetooth® transceiver, Wi-Fi®, etc.

Figure 4:
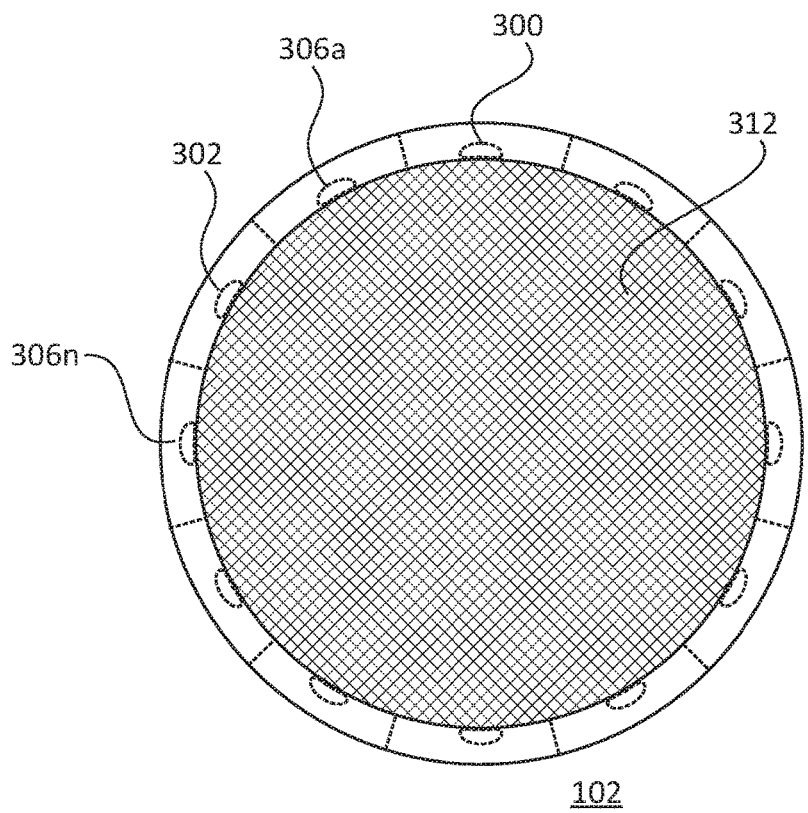
FIG. 4 is a cross-sectional view of a speaker of the medical attachment device of FIG. 3 at section A-A in accordance with the present invention.

With reference to FIGS. 1, 3, and 4, the processor 122 further comprises a sound database 124 communicatively coupled to a speaker 312 disposed on the medical attachment device 102. In other embodiments, the sound database 124 may be communicatively coupled to another device that allows the diaphragm of stethoscope 103 to vibrate. In one embodiment, the speaker 312 is disposed in a direction toward the stethoscope diaphragm in embodiments using the stethoscope 103. In other embodiments, the speaker 312 may be placed at alternative locations on the medical attachment device 102.

The sound database 124 includes a plurality of biological sounds representing, without limitation, medical conditions such as breathing, heart, abdominal, etc. The processor 122, in combination with a wired or wireless connection, is configured to determine the location of the medical attachment device 102 relative to the subject 112 and thereafter stream a biological sound to the speaker 312 which corresponds to the location of the medical attachment device 102 relative to the subject 112. In one exemplary, non-limiting embodiment, when the medical attachment device 102 is located close to the subject's 112 heart, a heartbeat sound will stream from the processor 122 to the medical attachment device 102, more specifically, the speaker 312. Advantageously, this eliminates the need for an independent onlooker, such as a teaching instructor, to monitor the auscultation training and emit the appropriate sound at the appropriate time, depending on the location of the medical attachment device 102 relative to the subject 112. In one exemplary embodiment, the medical attachment device 102 may include a rechargeable or non-rechargeable battery configured to power the medical attachment device 102.

Figure 5:
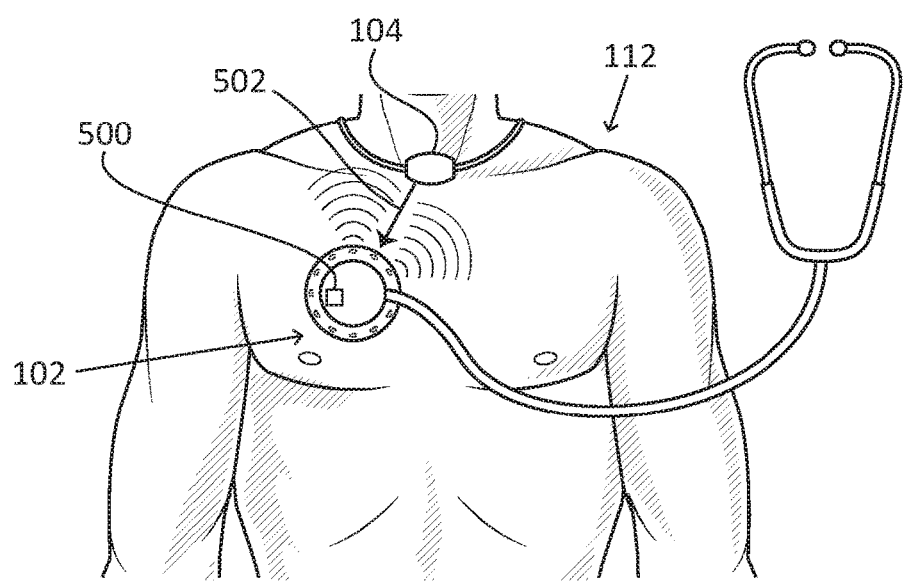
FIG. 5 is an elevational front view of an orientation sensor of the medical attachment device of FIG. 1 disposed near the subject's chest in accordance with the present invention.
Figure 6:
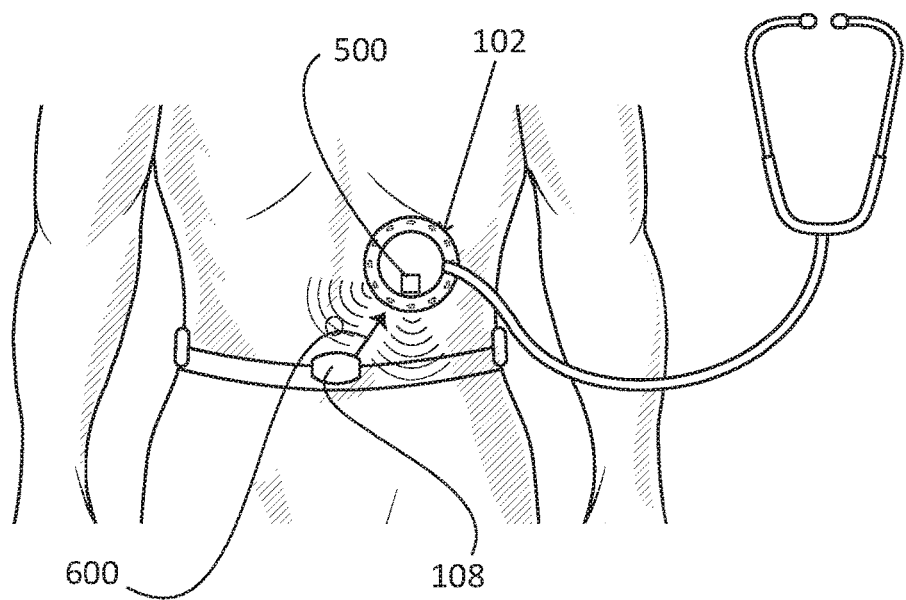
FIG. 6 is an elevational front view the orientation sensor of the medical attachment device of FIG. 1 disposed near the subject's abdomen in accordance with the present invention.

With reference now to FIGS. 5 and 6, an orientation sensor 500 is shown coupled to the medical attachment device 102. In one embodiment, the orientation sensor 500 is an X-Y-Z axis accelerometer. The orientation sensor 500 is configured to sense an orientation of the medical attachment device 102 relative to gravity. More specifically, because the medical attachment device 102 may be placed at any rotation, it would be difficult, if not virtually impossible, to determine at which one of the reflectors 104, 108 the light signal is emitting from. For example, depending on the rotation, placing the medical attachment device 102 over the subject's 112 right chest (FIG. 5) may produce a signal 502 that is the same or similar to a signal 600 generated when the medical attachment device 102 is placed over the subject's 112 left abdomen (FIG. 6). The orientation sensor 500 generates data communicated to the processor 122 (FIG. 1) through, for example, the wireless transmitter/receiver 310 (FIG. 3), in order to calculate the direction of gravity. Said another way, the tracking system 100 determines whether the signal reflection is coming from the first reflector 104 located near the subject's 112 chest, or the lower second reflector 108 located near the subject's 112 abdomen. In one embodiment, the tracking system 100 also utilizes data from the processor's accelerometer, for example through a software program installed on the processor 122, to determine the body position of the subject 112 and thus know where to expect (i.e., chest, back, abdomen, etc.) the medical attachment device 102 relative to the subject 112 as per commonly accepted medical examination practices.

In one embodiment, breathing synchronization may be accomplished by using a real-time stream of data, e.g., from the orientation sensor 500, to the processor 122 (FIG. 1) through the wired or wireless connection. More specifically, as the subject's 112 chest expands and contracts during inhalation and exhalation, respectively, the signals of the orientation sensor 500 on the medical attachment device 102 change. In one embodiment, in response to the signal change, the orientation sensor 500 may utilize the signals to track the real breathing cycle of the subject 112 and synchronize the breathing cycle of the sound database 124 to that of the subject 112. In other embodiments, a software program installed on the processor 122 (FIG. 1) may utilize the signals to track the real breathing cycle of the subject 112 and synchronize the breathing cycle of the sound database 124 to that of the subject 112.

Figure 7:
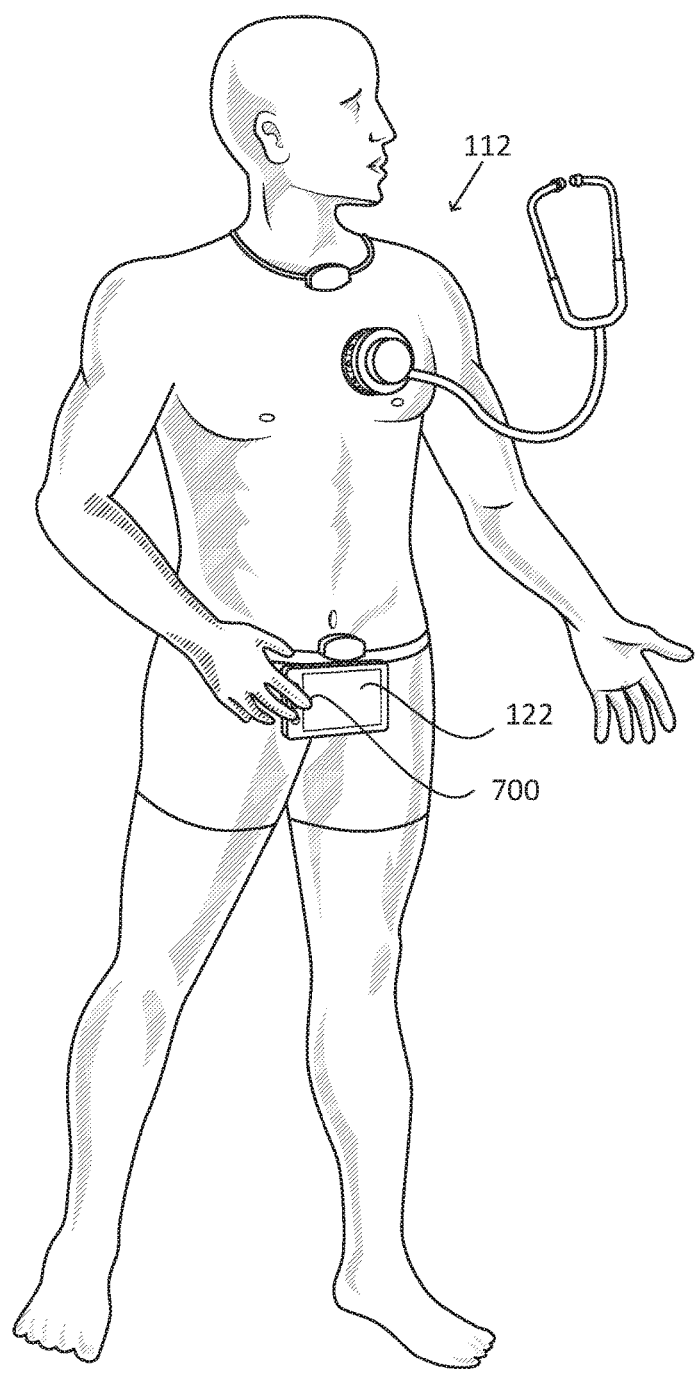
FIG. 7 is an elevational front view of a processor of the tracking system of FIG. 1 configured to detect a pulse of the subject.

With reference now to FIG. 7, pulse synchronization may be accomplished by the subject 112 placing a single finger 700 over a camera of the processor 122. In one embodiment, a software program installed on the processor 122 may detect the subject's 112 pulse signal through photoplethysmography. Generally speaking, a photoplethysmograph uses infrared sensors to detect skin color and/or volume changes that occur with each heartbeat. In other embodiments, pulse synchronization may be accomplished through other methods. In one embodiment, in use, such as during auscultation training, when the subject 112 sees that the trainee is listening to the subject's 112 heart, the subject 112 may be signaled to place the single finger over the camera of the processor 122 so that the pulse synchronization may be accomplished. In other embodiments, when the medical attachment device 102 is placed over the heart, the processor 122 signals the speaker 312 (FIG. 3) or another communication component, to vibrate, emit sound, or provide another form of communication to the subject 112, signaling the subject 112 to place a finger over the camera of the processor 122.

Figure 8:
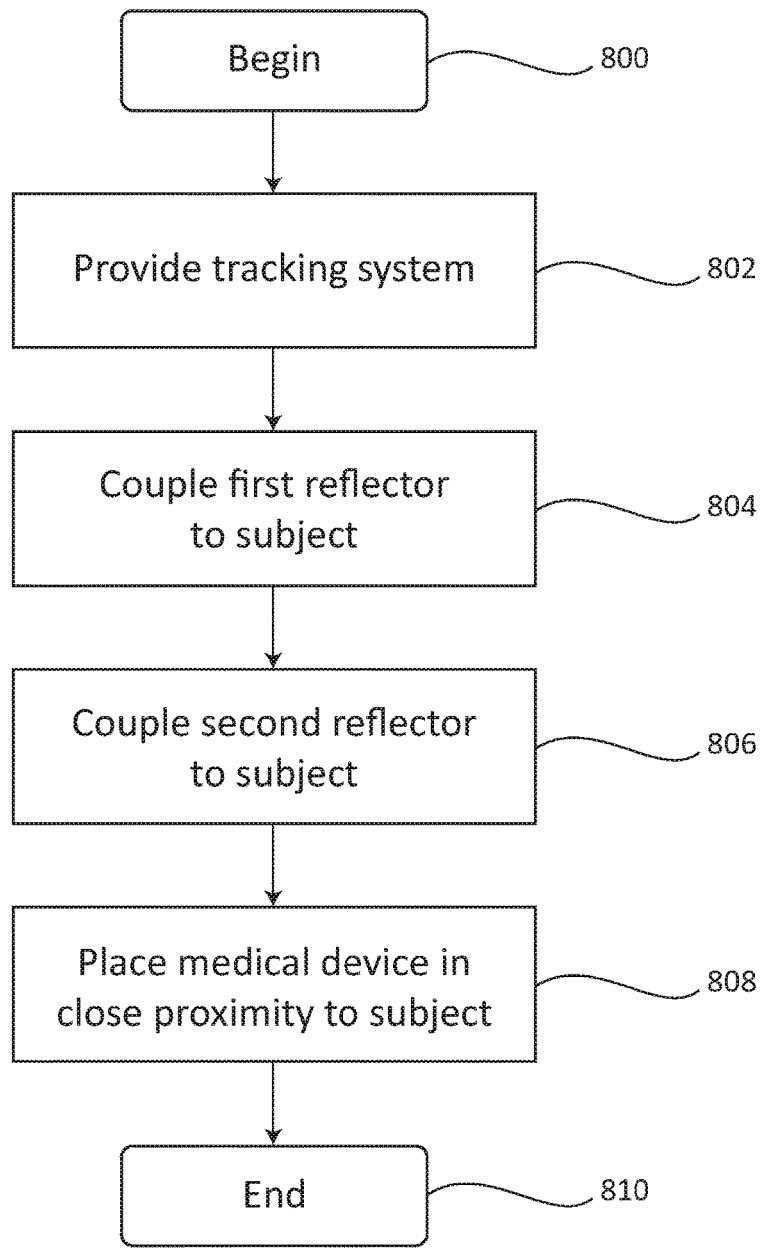
FIG. 8 is an exemplary process-flow diagram depicting a method of tracking a medical attachment device within a tracking area in accordance with one embodiment of the present invention.

Referring now to FIG. 8, in conjunction with FIGS. 1-7, there is provided an exemplary process-flow diagram depicting a method of tracking a medical attachment device within a tracking area. The steps delineated in the exemplary process-flow diagram of FIG. 8 are merely exemplary of the preferred order of tracking a medical attachment device within a tracking area, and said steps may be carried out in another order, with or without additional steps included therein.

In said process, the method begins at step 800 and immediately proceeds to the step 802 of providing, e.g., bringing into physical existence, a tracking system, such as the tracking system 100 of FIG. 1. The present method however, is not limited to use with the tracking system 100 but may also be used with other tracking systems as well.

In one embodiment, the tracking system 100 preferably, but not necessarily, includes the medical attachment device 102, the first and second reflectors 104, 108 defining the first and second tracking regions 106, 110, the reflector sensor 120, the light emitters 300, 302, the activation device 304, and the plurality of photodetectors 306a-n, described in detail above. In step 804, the first reflector 104 is coupled to the subject 112. In a preferred embodiment, the first reflector 104 is coupled to a necklace worn by the subject 112. In other embodiments, the first reflector 104 may be coupled to another article of clothing worn by the subject 112 or may be coupled directly to the subject 112. In step 806, the second reflector 108 is coupled to the subject 112. In a preferred embodiment, the second reflector 108 is coupled to a belt worn by the subject 112. In other embodiments, the second reflector 108 may be coupled to another article of clothing worn by the subject 112 or may be coupled directly to the subject 112.

In step 808, the medical attachment device 102 is placed in close proximity to the subject 112. As stated above, the term "close proximity" is defined herein as touching the subject 112 or within 2 inches of the subject 112. In other embodiments, the term close proximity may be outside of this range. Following placement of the medical attachment device 102 within close proximity to the subject 112, an activation device, such as the activation device 304 may be activated. As mentioned above, the activation device 304 may operate through a mechanical, resistive, capacitive, or optical system configured to detect when the medical attachment device 102 is placed in close proximity to the subject 112.

Following activation of the activation device 304, the light emitters 300, 302 emit light signals, e.g., pulses, in a direction toward the reflectors 104, 108. The light signals then reflect from the reflectors 104, 108 in a direction toward the reflector sensor 120. The reflector sensor 120 is operable to integrate the first and second reflectors 104, 108 in combination with a processor, such as the processor 122, and a wired or wireless connection, to determine a location of the medical attachment device 102 relative to the subject 112. During the method of tracking the medical attachment device 102, the subject 112 may be instructed to place a finger over a camera disposed on the processor to detect a pulse of the subject 112 when the medical attachment device 102 is positioned adjacent to a chest region of the subject 112, resulting in pulse synchronization. Breathing synchronization may also be accomplished, as described above.

In one embodiment, to deactivate the tracking system 100, the activation device 304 is moved a distance away from the subject 112. In one embodiment the distance is greater than 0.5 to 1.0 inch. In other embodiments, the distance may vary, as programmed by the trainee. The process ends at step 810.

Figure 9:
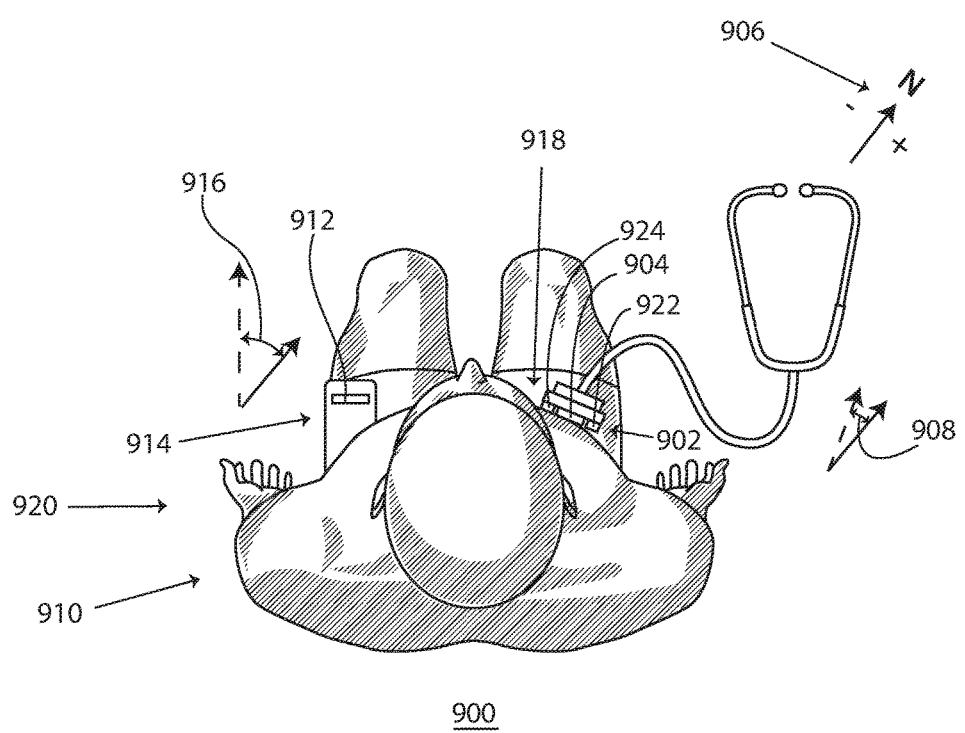
FIG. 9 is an elevational top plan view depicting a first magnetometer coupled to a medical attachment device and disposed on an anterior surface of a subject and a second magnetometer disposed near the subject.

With reference now to FIG. 9, a medical attachment device position detection system 900 is depicted in an elevational top plan view. In one embodiment, the medical attachment device position detection system 900 further improves the accuracy of the tracking system 100, through the use of at least two magnetometers, as described below. Said another way, in a preferred embodiment, the medical attachment device position detection system 900 includes the same or substantially the same features as the tracking system 100, in addition to the components described below. In other embodiments, the medical attachment device position detection system 900 may be used independent of the tracking system 100.

In one embodiment, the medical attachment device position detection system 900 includes a first and a second magnetometer coupled to a medical attachment device and a processor, respectively, and each configured to be positioned in close proximity to the subject. The first magnetometer is configured to produce data associated with an angle, e.g., an azimuth angle, of the medical attachment device and the second magnetometer is configured to produce data associated with an angle, e.g., an azimuth angle, of the processor. The term "azimuth" is defined herein as an angular measurement in a spherical coordinate system and includes the angle formed between Earth's magnetic north and a reference line extending from a select origin, as commonly understood by a person of ordinary skill in the art. The processor is operably configured to determine the first and second azimuth angles using the data provided by the first and second magnetometers. In the same vein, the processor is operably configured to compare the first and second azimuth angles using one or more formulas to determine the position of the medical attachment device relative to the subject. The position may be at least one of anterior, posterior, to the right of, and to the left of the subject. In one embodiment, once the position is determined, additional components of the tracking system 100, e.g., the reflectors, reflector sensors, etc., may be used to pinpoint the exact location of the medical attachment device and an appropriate biological sound may be emitted by a speaker coupled to the medical attachment device.

The first example of the medical device position detection system 900, as shown in FIG. 9, includes a medical attachment device 902. FIG. 9 depicts the medical attachment device 902 as an attachment to a standard diaphragm of a stethoscope, e.g., a disc. In other embodiments, the medical attachment device 902 may be fixedly coupled to the diaphragm of a stethoscope or may be provided in various other sizes and shapes complimentary to the stethoscope or another medical diagnostic tool.

In one embodiment, in addition to incorporating the features described with respect to the trackable medical attachment device 102, the medical attachment device 902 includes a first magnetometer 904 coupled to thereto. In one embodiment, the first magnetometer is a 3-axis magnetometer configured to orient the first magnetometer 904 and the medical attachment device 902 with respect to Earth's magnetic north 906. More specifically, the first magnetometer 904 is configured to provide data in the form of the x, y, and z values so that a processor 914 may calculate a first angle 908. In a preferred embodiment, the first angle 908 is a first azimuth angle of the medical attachment device 902 with respect to Earth's magnetic north 906. In other embodiments, the first angle 908 may be another type of angle. In the same vein, in other embodiments, the first magnetometer 904 may be an alternative type of magnetometer and the data may include other values.

FIG. 9 depicts the device position detection system 900 including a second magnetometer 912. In one embodiment, the second magnetometer 912 is communicatively coupled to the processor 914. FIG. 9 depicts the processor 914 as a smartphone, however the processor may be another suitable electronic device, such as a personal digital assistant, a computer, or the like. In a preferred embodiment, the processor 914 includes the same or substantially the same features as the processor 122 describe above. In other embodiments, the processor 914 may include different features than the processor 122.

Figure 10:
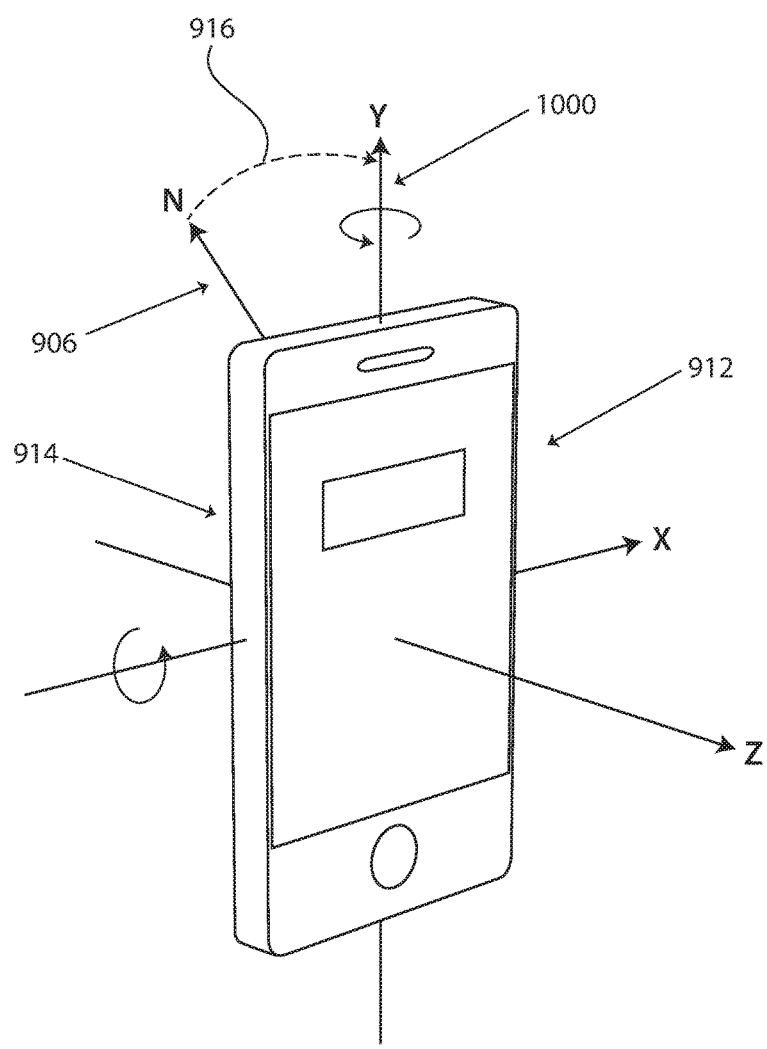
FIG. 10 is a perspective view of the second magnetometer coupled to a processor in accordance with the present invention.

With brief reference to FIGS. 9 and 10, in one embodiment, the second magnetometer 912 is a 3-axis magnetometer. The second magnetometer 912 is configured to orient the processor 914 with respect to Earth's magnetic north 906. In one embodiment, the second magnetometer 912 is configured to provide data in the form of the x, y, and z values of the second magnetometer 912 so that the processor 914 may calculate a second angle 916. The term "data" is defined herein as information, such as coordinates, measurements, and the like, used to calculate or analyze at least one of the first angle and the second angle. In a preferred embodiment, the second angle 916 is a second azimuth angle of the processor 914 with respect to Earth's magnetic north 906. In other embodiments, the second angle 916 may be another type of angle. With specific reference to FIG. 10, the second angle 916 is the angle formed between the y-axis 1000 and Earth's magnetic north 906. In other embodiments, the second magnetometer 912 may be an alternative type of magnetometer and the data may include other values.

Figure 14:
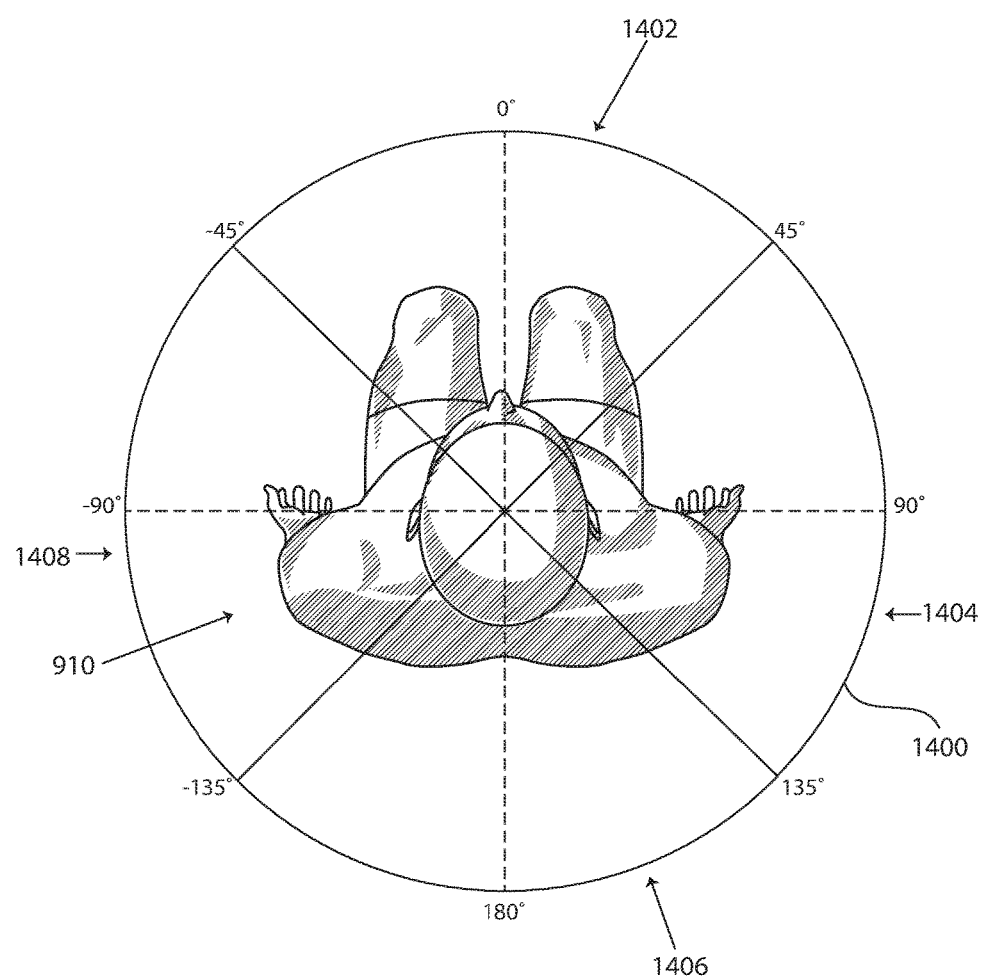
FIG. 14 is an elevational top plan view depicting a measurement circle and a plurality of coordinate regions in accordance with the present invention.

With reference again to FIG. 9, the first and second angles 908, 916 are compared by the processor 914, using or more formulas to determine the position of the medical attachment device 902 relative to the subject. With brief reference to FIG. 14, in one embodiment, the position may be determined by dividing a measurement circle 1400 surrounding the subject 910 into one or more coordinate regions, with each coordinate region corresponding to one of the four positions mentioned above, i.e., the anterior, posterior, right side, and left side positions.

For example, in one non-limiting embodiment, using the processor 914 (FIG. 9) as a zero reference point, the measurement circle may be divided into coordinate regions using a first coordinate region 1402 between −45 and +45 degrees, a second coordinate region 1404 between +45 degrees and +135 degrees, a third coordinate region 1406 between +135 degrees and −135 degrees, and fourth coordinate region 1408 between −135 degrees and −45 degrees. When the difference between the first and second angles 908, 916 falls within the first coordinate region 1402, the processor is configured to determine that the medical attachment device 902 is disposed on an anterior surface of the subject 910. In the same vein, when the difference between the first and second angles 908, 916 falls within the second coordinate region, the medical attachment device 902 is disposed on a right side of the subject. When the difference falls within the third coordinate region, the position is a posterior surface of the subject and if the difference falls within the fourth coordinate region, the position is on a left side of the subject.

In another embodiment, the measurement circle 1400 may be divided into coordinate regions between −60 and +60 degrees (anterior surface), +60 degrees and +120 degrees (right side), +120 degrees and −120 degrees (posterior surface), and −120 degrees and −60 degrees (left side). In the aforementioned embodiments, the first angle 908 and the second angle 916 are between approximately −180° to +180°. In other embodiments, the first and second angles 908, 916 may be outside of this range. It is to be understood that the coordinate regions provided herein are provided for illustrative purposes only and are not intended to be limiting. In other embodiments, other coordinate regions may be provided and are within the scope of the present invention.

With reference again to FIG. 9, the first angle 908 is depicted as being approximately −30° and the second angle 916 is depicted as being approximately −45°. The processor 914 is operably configured to determine that the medical attachment device 902 is on an anterior surface 918 of the subject because the difference between the first angle 908 and the second angle 916 falls between −45° and +45°. Further illustrative examples are provided herein with respect to FIGS. 11-12.

In a preferred embodiment, the first and second magnetometers 904, 912 are used in combination with the orientation sensor 500 described above with respect to FIG. 5, to detect the position of the medical attachment device 902 FIG. 9 relative to the subject 910. In a preferred embodiment, the subject 910 is a simulated patient, a standard patient, an animal, or another person participating in auscultation training. In another embodiments, the subject 910 may be a mannequin, although a living person is preferred to provide a more realistic setting during auscultation training.

In order to communicate with the processor 914, in embodiments in which the medical device position detection system 900 includes a wireless connection, the medical attachment device 902 includes a wireless transmitter/receiver 924 communicatively coupled to the processor 914. The wireless transmitter/receiver 924 is operably configured to transmit the data, e.g., the x, y, and z coordinates, generated by the first magnetometer 904 to the processor to calculate the first angle 908. The wireless transmitter/receiver 924 may operate using a radio transmitter, Bluetooth® transceiver, Wi-Fi®, etc. In other embodiments, a wired connection may be used to communicate the data generated by the first magnetometer 904 to the processor 914.

Figure 11:
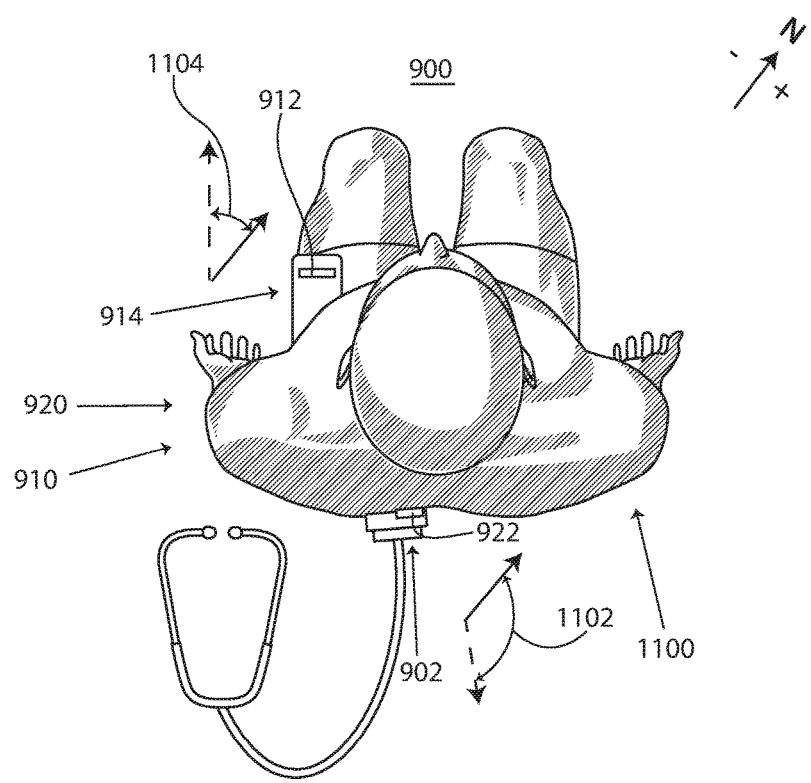
FIG. 11 is an elevational top plan view depicting the first magnetometer of FIG. 9 coupled to the medical attachment device and disposed on a posterior surface of the subject and the second magnetometer disposed near the subject in accordance with the present invention.
Figure 12:
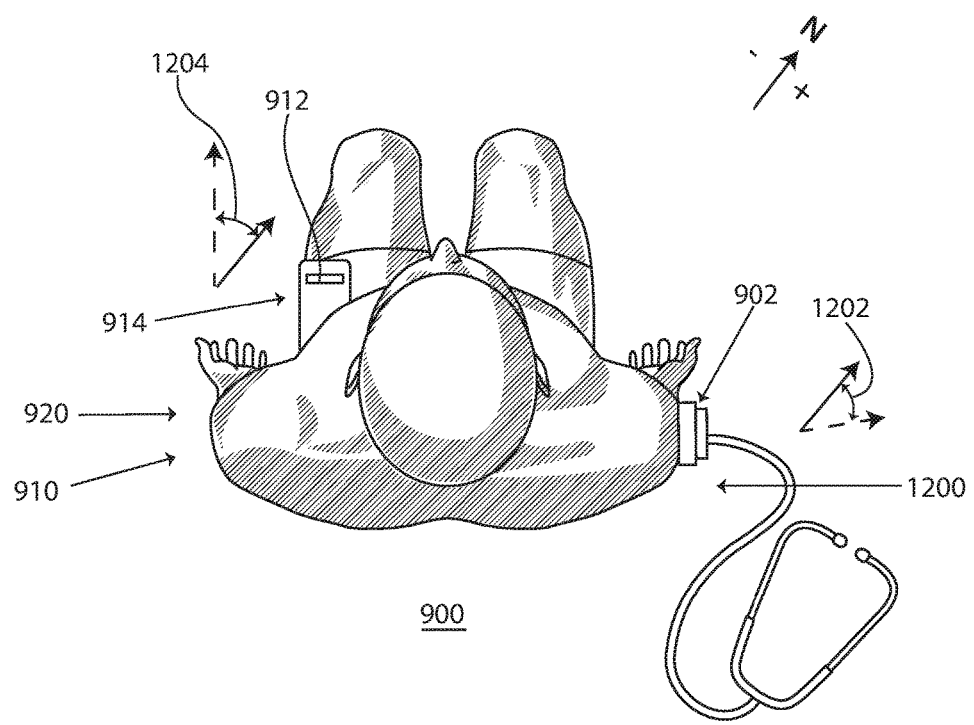
FIG. 12 is an elevational top plan view depicting the first magnetometer of FIG. 9 coupled to the medical attachment device and disposed on a right side of the subject and the second magnetometer disposed near the subject.
Figure 13:
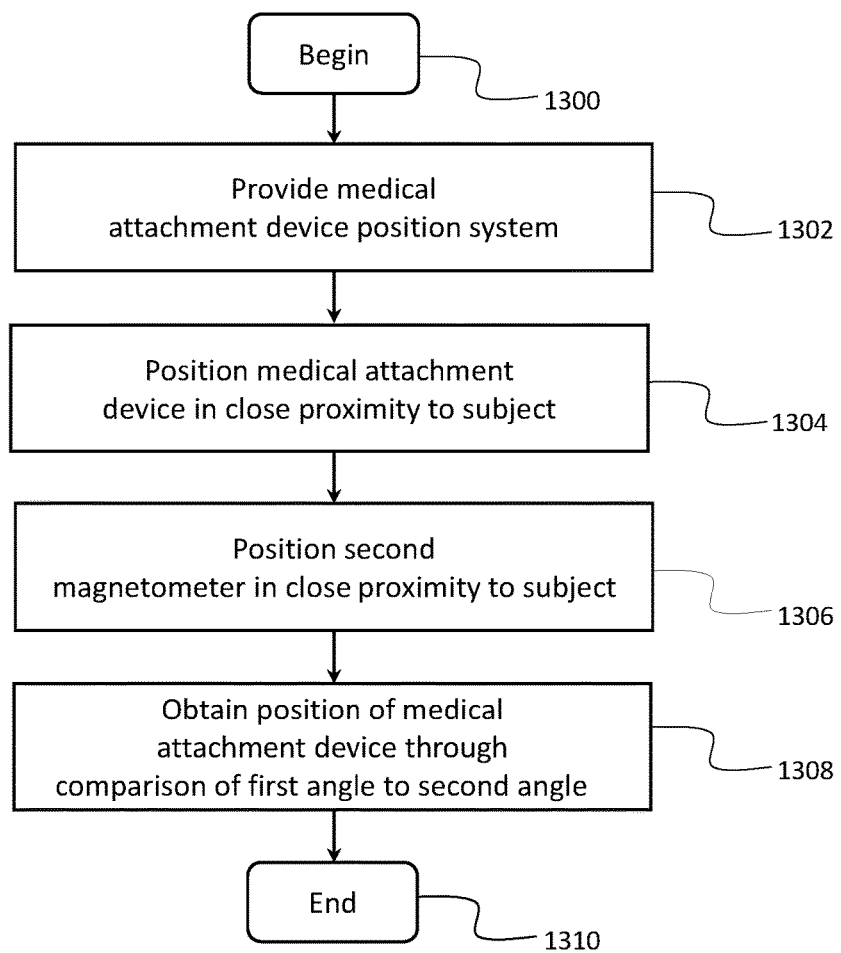
FIG. 13 is an exemplary process-flow diagram depicting a method of determining a position of a medical attachment device relative to the subject in accordance with one embodiment of the present invention.

Referring now to FIG. 13, in conjunction with FIGS. 9-12, there is provided an exemplary process-flow diagram depicting a method of detecting a position of a medical attachment device, such as the medical attachment device 902, relative to the subject 910, for use during medical training. As mentioned above, the position of the medical attachment device 902 relative to the subject 910 may be at least one of anterior to the subject 910, posterior to the subject 910, on a right side of the subject 910, and on a left side of the subject 910. In use, once the position of the medical attachment device 902 is determined, a biological sound may be emitted from the speaker 922 coupled to the medical attachment device 902. The biological sound represents a medical condition that may be experienced by the subject 910. The steps delineated in the exemplary process-flow diagram of FIG. 13 are merely exemplary of the preferred order of detecting a position of a medical attachment device relative to the subject 910 and the steps may be carried out in another order, with or without additional steps included therein.

In said process, the method begins at step 1300 and immediately proceeds to the step 1302 of providing a medical device position detection system 900, such as the medical device position detection system 900 of FIG. 9. The present method however, is not limited to use with the medical device position detection system 900 but may also be used with other positioning and/or tracking systems as well.

In step 1304, in one embodiment, the method includes positioning the medical attachment device 902 having the first magnetometer 904 coupled thereto adjacent or within close proximity to, i.e., near, the subject 910. In one non-limiting embodiment, as mentioned above, the term "close proximity" includes approximately 0-5 inches of the subject 910. The terms adjacent and close proximity are not intended to be limited to a defined distance and are intended to include any distance in which the components described herein are placed near the subject 910 while maintaining their described function.

In order to provide comprehensive auscultation training, the medical attachment device 902 may be positioned in various locations around the subject 910. For example, FIG. 9 depicts the medical attachment device 902 on an anterior surface 918, i.e., the front surface of the subject 910. FIG. 11 depicts an elevational top plan view of the medical attachment device 902 on a posterior surface 1100, i.e., rear surface, of the subject 910. FIG. 12 depicts an elevational top plan view of the medical attachment device 902 on a right side 1200 of the subject 910. In the same vein, the medical attachment device 902 may also be positioned on a left side of the subject (not shown).

In step 1306, in one embodiment, the method includes positioning the second magnetometer 912 adjacent the subject 910. In a preferred embodiment, the second magnetometer 912 is communicatively coupled to the processor 914. In the exemplary embodiments of FIGS. 9 and 11-12, the second magnetometer 912 and the processor 914 are positioned on a left side 920 of the subject 910, however such embodiments are provided for illustrative purposes only and are not intended to be limiting. In one embodiment, the second magnetometer 912 may be placed within the subject's 910 pocket, e.g., the right side or left side pocket, to conceal the second magnetometer 912 and further enhance the realism of the auscultation training. In other embodiments, the second magnetometer 912 may be positioned in front of or to the rear of the subject 910.

In step 1308, after the first and second magnetometers are positioned adjacent to the subject 910, the position of the medical attachment device 902 relative to the subject 910, i.e., anterior, posterior, right side, or left side, may be obtained via the processor 914 comparing the first angle 908 to the second angle 916. In one embodiment, a software program may be installed in the processor 914 to compare the first angle 908 to the second angle 916. In other embodiments, the processor 914 may include an alternative type of program or other suitable system operable to compare the first and second angles 908, 916 and calculate the position of the medical attachment device 902.

In one embodiment, in addition to the position of the medical attachment device 902 being detected by comparing the first angle 908 to the second angle 916, data provided by the orientation sensor 500, e.g., an accelerometer, may also be used. For example, in order to determine whether the subject 910 is lying down, sitting upright, sitting upright at an angle, laying on the right side, or laying on the left side, the first angle 908 may be compared to the second angle 916 and the data provided by the accelerometer 500. In other embodiments, the determination as to whether the subject 910 is lying down, sitting up, sitting upright at an angle, laying on the right side, or laying on the left side, may be determined using additional or other types of data.

In order to further detect the position of the medical attachment device 902 relative to the subject 910, additional components of the tracking system 100, e.g., the reflectors, reflector sensors, etc., may be used to pinpoint the exact location of the medical attachment device 902 relative to the subject 910, as per commonly accepted medical examination practices. Once the position of the medical attachment device 902 is determined, the speaker 922 disposed on the medical attachment device 902 may emit the appropriate biological sound from a sound database coupled to the processor 914, in the manner described above with respect to the sound database 124 and the processor 122.

With reference to FIG. 11, an example implementation of the present method and the medical device position detection system 900 is described for illustrative purposes. FIG. 11 depicts an elevational top plan view of the medical attachment device 902 in a first position, i.e., a posterior surface 1100 of the subject 910. In the first position depicted in FIG. 11, a first angle 1102, i.e., first azimuth angle, is approximately +120° and a second angle 1104, i.e., second azimuth angle, is approximately −45°. The processor 914 is operably configured to determine that the medical attachment device 902 is positioned on the posterior surface 1100 of the subject 910 because the difference between first angle 1102 and the second angle 1104 is more than +135°. As such, the speaker 922 may emit the biological sound that would commonly be heard by the trainee when examining the posterior surface 1100 of the subject 910.

With reference to FIG. 12, the medical attachment device 902 is shown in a second position, i.e., a right side 1200, of the subject 910. Although FIG. 12 depicts the medical attachment device 902 adjacent the subject's 910 right shoulder, it is to be understood that such illustration is provided for exemplary purposes only. In a preferred embodiment, the medical attachment device 902 is to be positioned underneath the subject's 910 arm at a location adjacent the subject's 910 rib cage. In other embodiments, the medical attachment device 902 may be positioned at other locations on the subject's right side 1200.

In the second position depicted in FIG. 12, a first angle 1202, i.e., first azimuth angle, is approximately +45° and a second angle 1204, i.e., second azimuth angle, is approximately −45°. The processor 914 is operably configured to determine that the medical attachment device 902 is positioned on the right side 1200 of the subject 910 because the difference between the first angle 1202 and the second angle 1204 is greater than +45° but less than +135°. As such, the speaker 1106 may emit the biological sound that would commonly be heard by the trainee when examining the right side 1200 of the subject 910. In the same vein, if the difference between the first angle 1202 and the second angle 1204 were less than −45° but more than −135°, the medical device position detection system 900 is operably configured to determine that the medical attachment device 902 is on the left side of the subject 902 (not shown). It is to be understood that nominal deviations, for example, between +/−5-10 degrees, are within the scope of the present invention. It is also to be understood that the examples and formulas provided herein are for illustrative purposes only and not intended to be limiting. The process ends at step 1310.

A medical attachment device position detection system for use during medical training has been disclosed that features a first magnetometer and a second magnetometer configured to determine an angle of a medical attachment device and a processor, respectively. The angles may be compared by a processor in order to obtain a position of the medical attachment device relative to the subject so that an appropriate biological sound may be emitted by a speaker coupled to the medical attachment device.

What is claimed is:

1. A medical attachment device position detection system for use during medical training comprising:
   a processor;
   a sound database communicatively coupled to the processor and including a plurality of sound files configured to represent a subject's medical condition;
   a medical attachment device coupled to a stethoscope and communicatively coupled to the processor;
   a speaker coupled to the medical attachment device;
   a first magnetometer coupled to the medical attachment device, the first magnetometer configured to produce data associated with a first angle; and
   a second magnetometer configured to produce data associated with a second angle, the second magnetometer communicatively coupled to the processor, the processor operably configured to compare a relationship of the first angle relative to the second angle to determine a position of the medical attachment device relative to the subject, the position corresponding to one of the plurality of sound files in the sound database.

2. The medical attachment device position detection system according to claim 1, wherein:
   the medical attachment device includes an orientation sensor coupled thereto.

3. The medical attachment device position detection system according to claim 1, wherein:
   the second magnetometer is a 3-axis magnetometer.

4. The medical attachment device position detection system according to claim 1, wherein:
   the processor and the second magnetometer are each housed within an electronic device.

5. The medical attachment device position detection system according to claim 1, wherein:
   the position of the medical attachment device relative to the subject is at least one of anterior to the subject, posterior to the subject, disposed on a right side of the subject, and disposed on a left side of the subject.

6. The medical attachment device position detection system according to claim 1, wherein:
   the first angle is between approximately −180° to +180°.

7. A method of detecting a position of a medical attachment device relative to a subject, the method comprising:
   providing a medical attachment device position detection system comprising:
      a processor;
      a sound database communicatively coupled to the processor and including a plurality of sound files configured to represent a subject's medical condition;
      a medical attachment device coupled to a stethoscope and communicatively coupled to the processor;
      a speaker coupled to the medical attachment device;
      a first magnetometer coupled to the medical attachment device, the first magnetometer configured to produce data associated with a first angle; and
      a second magnetometer configured to produce data associated with a second angle, the second magnetometer communicatively coupled to the processor, the processor operably configured to compare a relationship of the first angle relative to the second angle to determine a position of the medical attachment device relative to the subject, the position corresponding to one of the plurality of sound files in the sound database;
   positioning the first magnetometer in close proximity to the subject;
   positioning the second magnetometer in close proximity to the subject; and
   comparing the first angle from the first magnetometer to the second angle from the second magnetometer to obtain the position of the medical attachment device relative to the subject.

8. The method according to claim 7, wherein:
   the second magnetometer is a 3-axis magnetometer.

9. The method according to claim 7, wherein:
   the processor and the second magnetometer are each housed within an electronic device.

10. The method according to claim 9, further comprising:
    positioning the electronic device in close proximity to a side of the subject.

11. The method according to claim 7, further comprising:
    positioning the medical attachment device relative to at least one of anterior to the subject, posterior to the subject, on a right side of the subject, and on a left side of the subject.

12. The method according to claim 7, further comprising:
    positioning the medical attachment device within a first position relative to the subject;
    causing the speaker to emit a first sound from the sound database, the first sound corresponding to the first position;
    positioning the medical attachment device within a second position relative to the subject; and
    causing the speaker to emit a second sound from the sound database, the second sound corresponding to the second position.

13. The method according to claim 7, wherein:
    the medical attachment device includes an orientation sensor coupled thereto.

14. The method according to claim 7, further comprising:
    providing a plurality of coordinate regions corresponding to the position of the medical attachment device relative to the subject.

* * * * *